United States Patent [19]

Van Peppen

[11] 4,410,741

[45] Oct. 18, 1983

[54] PROCESS FOR MANUFACTURE OF CYCLOHEXANOL FROM PHENOL

[75] Inventor: Jan F. Van Peppen, Chester, Va.

[73] Assignee: Allied Corporation, Morris Township, Morris County, N.J.

[21] Appl. No.: 354,471

[22] Filed: Mar. 3, 1982

[51] Int. Cl.$^3$ ............................................... C07C 35/08
[52] U.S. Cl. ................................................. 568/835
[58] Field of Search ........................................ 568/835

[56] References Cited

U.S. PATENT DOCUMENTS 4,258,268  3/1981  Bjornson ............................. 568/835

FOREIGN PATENT DOCUMENTS 1115477  3/1969  United Kingdom ................ 568/835

*Primary Examiner*—Werren B. Lone
*Attorney, Agent, or Firm*—Richard A. Anderson

[57] ABSTRACT

In the process of phenol hydrogenation to cyclohexanol, improved yields of cyclohexanol are obtained by maintaining a hydrogen atmosphere throughout the entire operation. Of particular importance is that the hydrogen atmosphere is maintained during the time period when the nickel catalyst is allowed to settle and prior to decantation of the clear liquids.

5 Claims, No Drawings

PROCESS FOR MANUFACTURE OF CYCLOHEXANOL FROM PHENOL

BACKGROUND OF THE INVENTION

This invention relates to an improvement in the nickel-catalyzed hydrogenation of phenol to cyclohexanol by maintaining hydrogen atmosphere throughout the process, including the final phase, separation of catalyst.

The manufacture of cyclohexanol by hydrogenation of phenol with nickel catalyst is known in U.S. Pat. No. 3,998,884 and particularly U.S. Pat. No. 2,794,056, both hereby incorporated by reference, in toto. In this patent application, by "hydrogen atmosphere" is meant pure hydrogen or mixtures of hydrogen with other gases so long as hydrogen is present in an amount over 10 percent by volume at 250 psig ($1.72 \times 10^6$ pascals) up to over 25 percent at atmospheric pressure. For example, a typical hydrogen atmosphere would be 75 percent $H_2$ and 25 percent $N_2$ at atmospheric pressure.

SUMMARY OF THE INVENTION

This invention is an improvement in the method of manufacture of cyclohexanol by hydrogenation of phenol in the presence of a nickel catalyst in an amount of about 2–10 percent by weight catalyst at a temperature of from about 100°–200° C. and a pressure of from about atmospheric to 250 psig ($1.72 \times 10^6$ pascals), then allowing the catalyst to settle and separating the catalyst from the reactant. The improvement comprises maintaining a hydrogen atmosphere during the entire time period the catalyst is in contact with reactant, particularly including during the time when catalyst is separated from the reactants, whereby yield of cyclohexanol is improved and yield of by-product cyclohexanone is decreased. Preferably, the method is conducted in a batch sequential manner employing at least one hydrogenation vessel at a temperature of between about 120° to 180° C. with agitation of reactant and catalyst suspended therein. Even more preferably, the temperature is between about 130° and 140° C. and agitation of the reactants and catalyst is terminated when the phenol content of the reaction mass is below 1 percent by weight. This invention permits the cyclohexanone content in the final reactants separated from the catalyst to be as low as below one-tenth percent by weight of the reaction mass.

DESCRIPTION OF THE PREFERRED EMBODIMENTS

Cyclohexanol (Naxol) is produced commercially in a batch-type process. In this process, phenol is reacted with hydrogen in the presence of nickel catalyst at a temperature of 135° C. The batch reaction was terminated when the phenol had reached a low level, approximately 1.0 percent, and the cyclohexanone was approximately 0.2 percent. Prior to this invention, terminating the batch consisted of displacing the hydrogen by flushing with nitrogen and then allowing the catalyst to settle without agitation for a period of about four hours. It was found that during this period of catalyst settling, the amount of cyclohexanone in the liquid increased from approximately 0.2 percent to approximately 0.8 percent. This increase in cyclohexanone content did not happen when at the end of the batch reaction the hydrogen was not displaced by nitrogen, but was maintained as the atmosphere during the period of catalyst settling. With this improved procedure, the cyclohexanone decreased during settling to <0.1 percent. Cyclohexanone is a most undesirable by-product since it is difficult to remove by distillation and therefore only small amounts of cyclohexanone present causes large cyclohexanol yield losses.

I claim:

1. In the batch-type method of manufacture of cyclohexanol by the hydrogenation of phenol in the presence of a nickel catalyst in an amount of about 2 to 10 percent by weight catalyst, at a temperature of from about 100° to 200° C. and a pressure of from about atmospheric to 250 psig ($1.72 \times 10^6$ pascals), with agitation of liquid phenol and catalyst suspended therein, then allowing the catalyst to settle and separating the catalyst from the reactants, the improvement comprising
   maintaining a hydrogen atmosphere during the entire period that catalyst is in contact with reactants, particularly including during the time when catalyst is separated from the reactants, whereby yield of cyclohexanol is improved and yield of by-product cyclohexanone is decreased.

2. The method of claim 1 wherein the method of manufacture is conducted in a batch sequential manner employing at least one hydrogenation vessel, a temperature of between about 120° to 180° C. with agitation of reactants and catalyst suspended therein.

3. The method of claim 2 wherein the temperature is between about 130° and 140° C. and agitation of the reactants and catalyst is terminated when phenol content of the reaction mass is below 1 percent by weight, whereby the cyclohexanone content in the final reactants separated from the catalyst is below 0.1 percent by weight.

4. The method of claim 3 wherein the hydrogen atmosphere is 60–85 percent by volume hydrogen and 15–40 percent by volume nitrogen.

5. The method of claim 1 wherein the hydrogen atmosphere contains over 25 percent by volume hydrogen at atmospheric pressure, and over as little as 10 percent by volume hydrogen as pressure increases up to 250 psig ($1.72 \times 10^6$ pascals).

* * * * *